United States Patent
Gunduz et al.

(10) Patent No.: US 6,391,906 B2
(45) Date of Patent: May 21, 2002

(54) CRYSTALS OF CELECOXIB

(75) Inventors: Halit Gunduz; Mehmet Bahar; Mehmet Goktepe, all of Istanbul (TR)

(73) Assignee: Fako Ilaclari, S.A., Istanbul (TR)

( * ) Notice: Subject to any disclaimer, the term of this patent is extended or adjusted under 35 U.S.C. 154(b) by 0 days.

(21) Appl. No.: 09/887,354

(22) Filed: Jun. 22, 2001

(30) Foreign Application Priority Data

Jun. 26, 2000 (TR) .......................... 2000/01872

(51) Int. Cl.[7] .................. A61K 31/415; A61P 29/00; C07D 231/12
(52) U.S. Cl. ...................... 514/406; 548/377.1
(58) Field of Search ................ 548/377.1; 514/406

(56) References Cited

FOREIGN PATENT DOCUMENTS

| WO | WO94/13635 | 6/1994 |
|----|------------|--------|
| WO | WO95/15316 | 6/1995 |
| WO | WO96/37476 | 11/1996 |
| WO | WO00/42021 | 7/2000 |
| WO | WO01/42222 | 6/2001 |

OTHER PUBLICATIONS

Penning, Thomas D. et al. Synthesis and Biological Evalation . . . , J. Med. Chem. (1997), 40(9), 1347–1366.

*Primary Examiner*—Robert W. Ramsuer
(74) *Attorney, Agent, or Firm*—Cowan, Liebowitz & Latman, P.C.; Michael I. Wolfson

(57) ABSTRACT

A new crystalline form of 4-[5-(4-Methylphenyl)-3-(trifluoromethyl)-1H-pyrazol-1-yl]benzenesulfonamide of Formula I

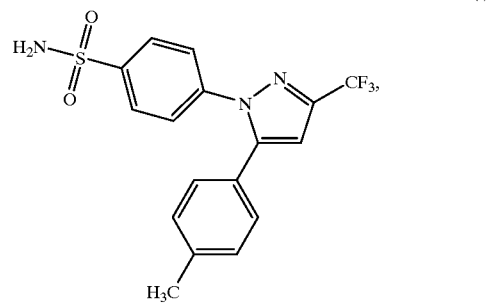

designated as Form I and a method for its production.

14 Claims, 4 Drawing Sheets

CRYSTALS OF CELECOXIB

BACKGROUND OF THE INVENTION

This invention relates to the pharmaceutical therapeutic agent 4-[5-(4-methylphenyl)-3-(trifluoromethyl)-1H-pyrazol-1-yl]benzenesulfonamide (celecoxib) of formula I

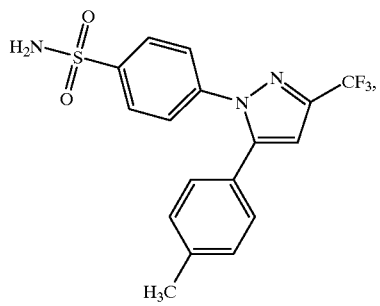

(I)

specifically to a new crystalline form of celecoxib with improved properties. This invention further relates to a method for the production of this crystalline form of the agent.

Since prostaglandins play a major role in the inflammation process, the discovery of non-steroidal anti-inflammatory drugs (NSAIDs) has focused on the inhibition of prostaglandin production, especially $PGG_2$, $PGH_2$ and $PGC_2$ production. The use of NSAIDs in the treatment of pain and swelling associated with the inflammation tends to cause side effects by affecting other prostaglandin regulated processes. Thus NSAIDs tend to cause significant side effects including ulcers.

Previous NSAIDs have been found to inhibit some enzymes including cyclooxygenase. Recently, an inducible form of cyclooxygenase associated with inflammation known as cyclooxygenase II (COX-2) or prostaglandin G/M synthase II has been found to exist. This enzyme is more effective in reducing inflammation, causing fewer and less drastic side effects.

Several compounds selectively inhibiting cyclooxygenase II are described in U.S. Pat. Nos. 5,380,738, 5,344,991, 5,393,790, 5,466,823, 5,434,178, 5,474,995, 5,510,368, and International Applications WO 96/06840, 96/03388, 96/03387, 95/15316, 94/15932, 94/27980, 95/00501, 94/13635, 94/20480 and 94/26731.

Certain substituted pyrazolylbenzenesulfonamides, specifically celecoxib (4-[5-(4-Methylphenyl)-3-(trifluoromethyl)-1H-pyrazol-1-yl]benzenesulfonamide) as selective COX-2 inhibitor and their preparation have been described in International Application WO 95/15316. In addition, an efficient preparation of 3-haloalkyl-1H-pyrazoles in a one-pot synthesis which is suitable for large-scale process has been described in International Application WO 96/37476.

International Application No. WO 00/32189 discloses specific celecoxib compositions. In this document a number of problems concerning the formulation of this agent, inter alia, its cohesiveness, low bulk density, low compressibility, poor solubility, etc., are described. According to this document, these disadvantages are caused by the crystal structure of celecoxib. Unformulated celecoxib, which has a crystal morphology that tends to form long cohesive needles, typically fuses into a monolith mass upon compression in a tablet die, which leads to problems in blending the agent uniformly. Further, low bulk density causes problems in processing the small quantities required in the formulation of pharmaceutical compositions.

SUMMARY OF THE INVENTION

It has now surprisingly been discovered that celecoxib may exist at least in two crystalline forms, hereinafter designated as Form I and Form II, having different properties.

Certain organic compounds can exist in several different crystal forms, which can have different chemical and physical properties, such as density, hardness, flow properties, etc. Therefore, new crystal forms of existing compounds are of great interest. The new crystal form of celecoxib reported herein provides improved properties, making it possible to overcome the problems described in the prior art. Since the new crystal form does not have the disadvantages of the known needle-like crystals, it overcomes the problems disclosed e.g. in WO 00/32189.

The object of the present invention, therefore, is to provide a new crystalline form of celecoxib which avoids the problems produced by the known, needle-like crystalline form. The solution of this object is provided by the new crystalline form of celecoxib as disclosed herein, which we have called "Form I" of celecoxib, and by the corresponding production method, as also described herein.

Still other objects and advantages of the invention will in part be obvious and will in part be apparent from the specification.

The invention accordingly comprises a composition of matter possessing the characteristics, properties, and the relation of constituents which will be exemplified in the composition hereinafter described, and the scope of the invention will be indicated in the claims.

BRIEF DESCRIPTION OF THE DRAWINGS

For a fuller understanding of the invention, reference is had to the following description taken in connection with the accompanying drawing(s), in which.

DESCRIPTION OF THE PREFERRED EMBODIMENTS

Crystalline forms are characterised by means of X-ray powder diffraction patterns. For this purpose a PHILIPS PW 1710 based diffractometer was used and Cu—$K_\alpha$-radiation ($\lambda(Cu—K_{\alpha 1})=1.54056$ Å; $\lambda(Cu—K_{\alpha 2})=1.54439$ Å) was applied. X-ray diffraction data are provided in terms of 2θ values and corresponding intensities.

The crystalline form of celecoxib designated as Form I according to the present invention is characterised by at least the X-ray powder diffractogram data given in table I:

TABLE I

X-ray Diffraction data of Form I:

| Angle [°2θ] | Rel. int [%] |
|---|---|
| 14.800 | 69.0 |
| 16.050 | 78.9 |
| 17.875 | 63.7 |
| 19.615 | 100.0 |
| 21.455 | 96.6 |
| 22.080 | 68.1 |
| 22.385 | 65.4 |
| 23.425 | 62.5 |
| 25.330 | 64.5 |
| 29.355 | 60.8 |

In a preferred embodiment of the present invention said crystalline form of 4-[5-(4-Methylphenyl)-3-(trifluoromethyl)-1H-pyrazol-1-yl]benzenesulfonamide of Form I is further characterised by at least the following further X-ray powder diffractogram data given in table II:

TABLE II

Further X-ray Diffraction data of Form I:

| Angle [°2θ] | Rel. int [%] |
|---|---|
| 10.670 | 33.4 |
| 10.970 | 34.0 |
| 12.985 | 32.4 |
| 13.855 | 17.5 |
| 18.340 | 40.4 |
| 18.685 | 40.0 |
| 20.425 | 19.1 |
| 20.670 | 19.0 |
| 23.185 | 48.7 |
| 24.510 | 37.8 |
| 24.930 | 34.5 |
| 25.730 | 22.8 |
| 26.915 | 23.1 |
| 27.630 | 31.5 |
| 28.185 | 26.2 |
| 29.955 | 32.7 |
| 30.375 | 9.9 |
| 31.405 | 9.6 |
| 34.915 | 15.7 |
| 35.585 | 10.9 |
| 37.895 | 17.9 |
| 44.070 | 9.4 |
| 45.250 | 14.5 |

(in addition to the dominant reflexes of table I).

Figure 1:
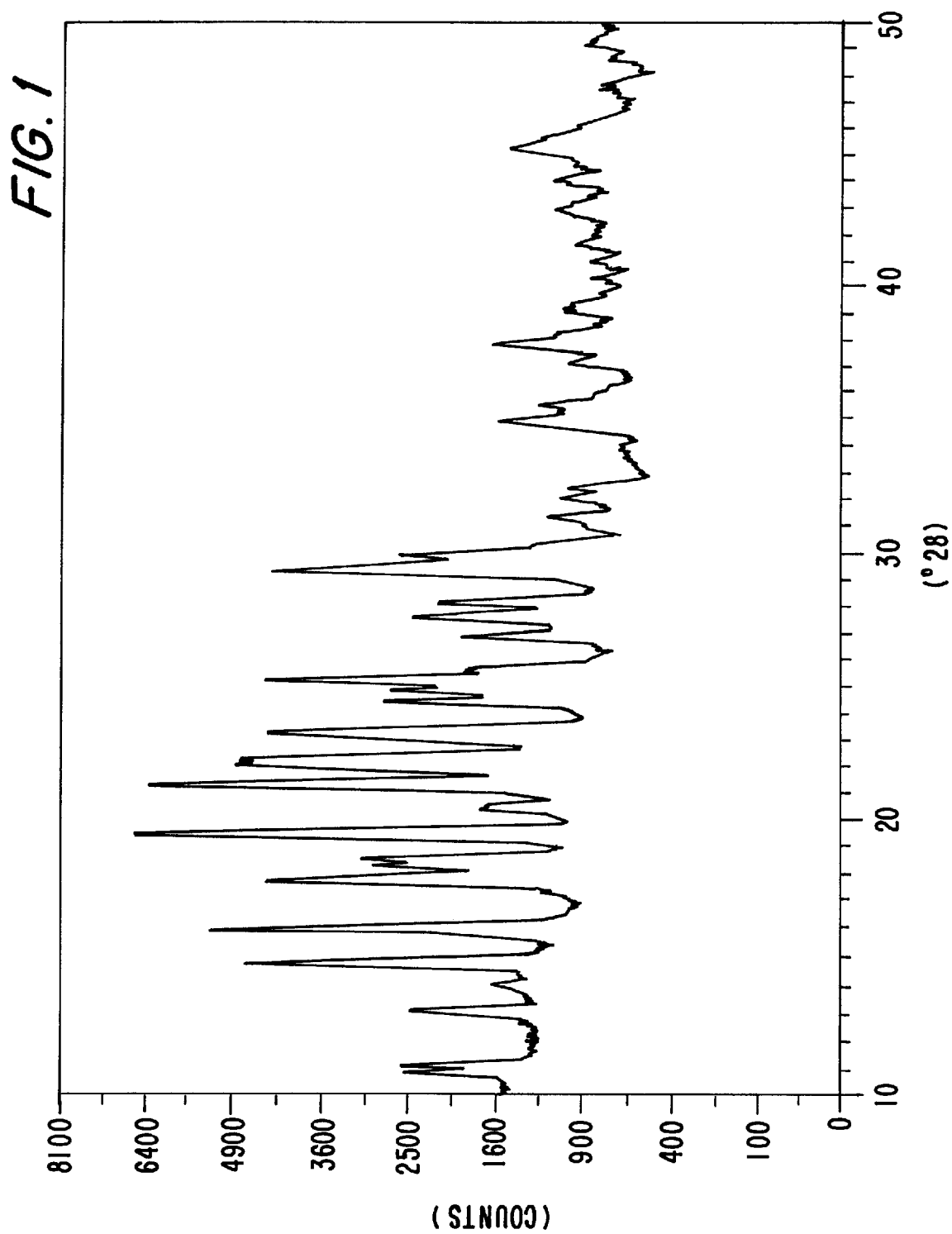
FIG. 1 is an x-ray diffraction pattern of the crystal of Form I of celecoxib prepared in accordance with the inventions.

An example of the X-ray diffraction pattern of Form I is shown in FIG. 1. The alternative disadvantageous, needle-like crystal form (designated herein as Form II) which is provided by the methods described in the prior art differs significantly from Form I according to the present invention.

Figure 2:
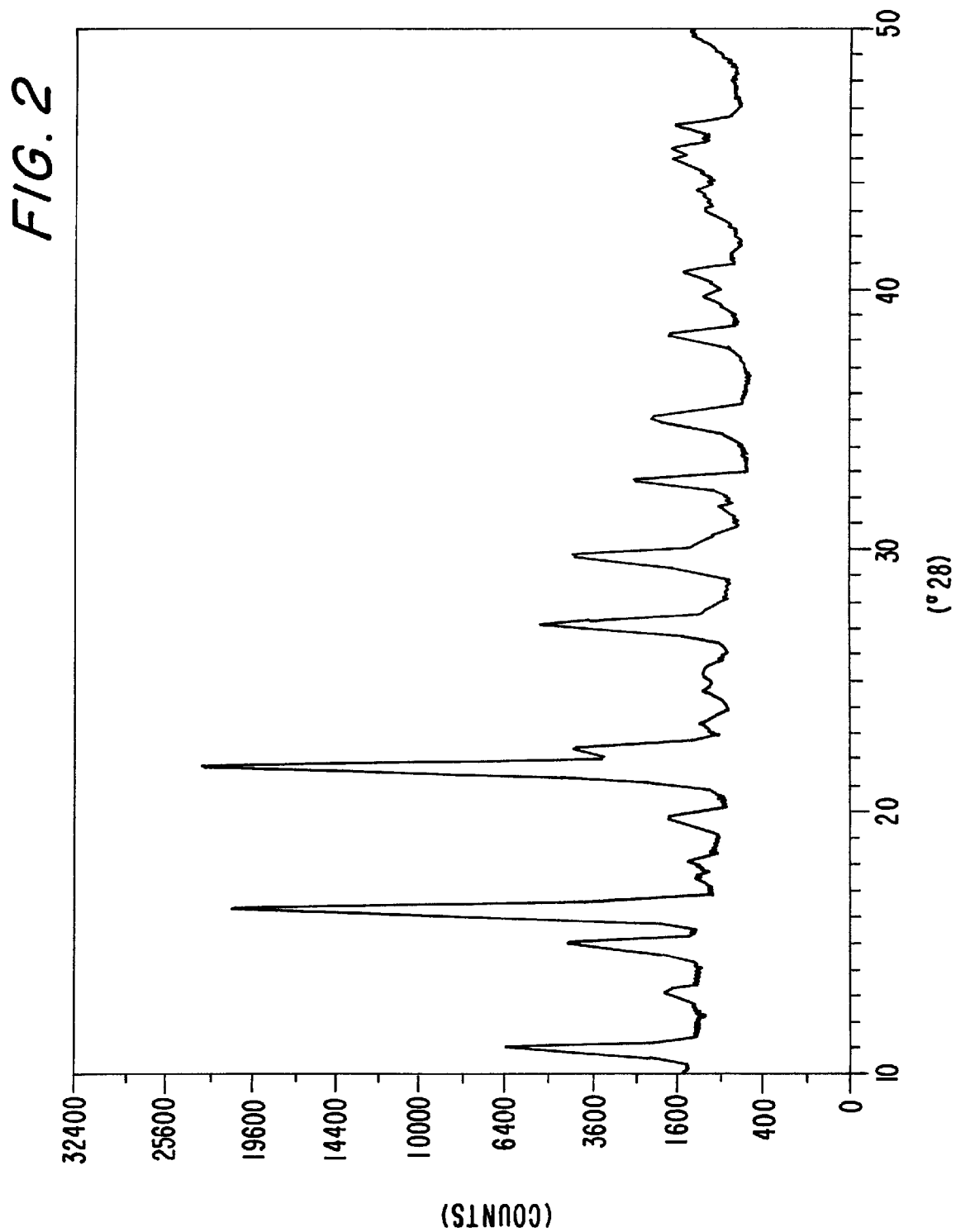
FIG. 2 is an x-ray diffraction pattern for the known Form II of Celecoxib.

An example of the X-ray diffraction pattern for the known Form II is shown in FIG. 2 and the corresponding data are given in Table III.

TABLE III

X-ray Diffraction data of Form II

| Angle [°2θ] | Rel. int [%] |
|---|---|
| 11.025 | 27.5 |
| 13.285 | 5.9 |
| 15.115 | 16.5 |
| 16.415 | 91.4 |
| 17.625 | 3.2 |

TABLE III-continued

X-ray Diffraction data of Form II

| Angle [°2θ] | Rel. int [%] |
|---|---|
| 18.265 | 3.6 |
| 19.785 | 5.6 |
| 21.820 | 100.00 |
| 22.440 | 16.9 |
| 23.500 | 2.7 |
| 24.620 | 3.0 |
| 25.460 | 2.7 |
| 27.280 | 21.0 |
| 29.885 | 15.6 |
| 31.580 | 1.5 |
| 32.815 | 9.0 |
| 35.185 | 7.4 |
| 38.205 | 5.8 |
| 38.415 | 4.2 |
| 39.695 | 2.5 |
| 40.740 | 3.7 |
| 41.285 | 0.8 |
| 42.960 | 2.4 |
| 43.810 | 2.7 |
| 44.820 | 4.5 |
| 45.415 | 5.0 |
| 46.300 | 4.9 |

Figure 3:
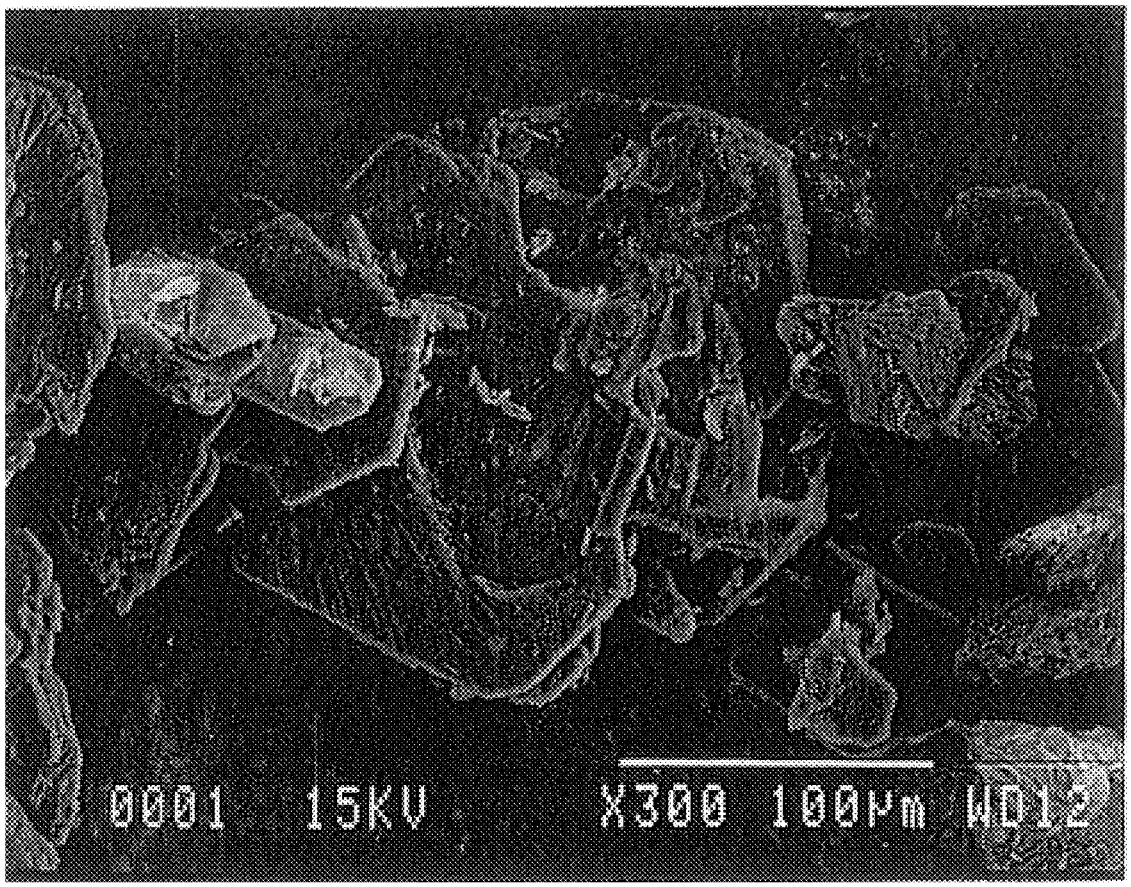
FIG. 3 is a SEM image of the crystallites of Form I described in FIG. 1.
Figure 4:
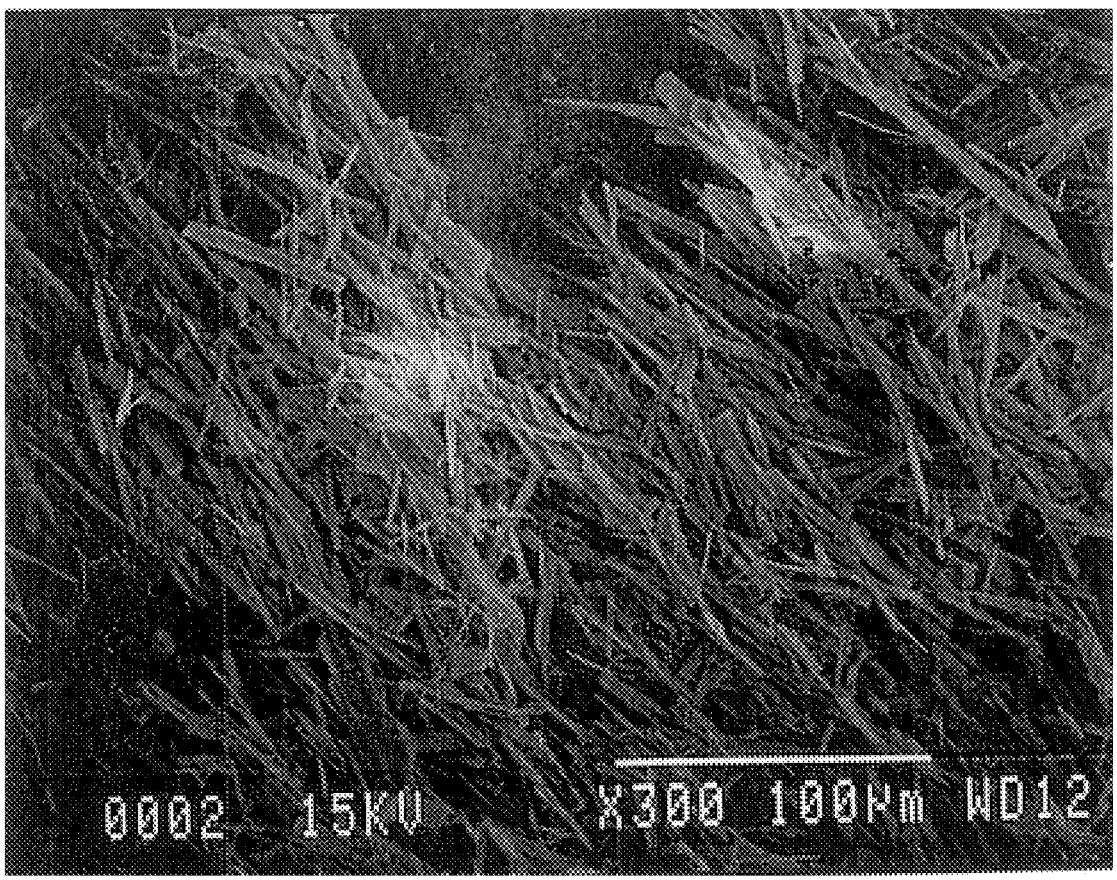
FIG. 4 is a SEM image of the crystallites of Form I described in FIG. 2.

Further, SEM images of the crystallites of Form I according to the invention and Form II obtained by the production methods known in the prior art clearly illustrate the plate like habit of the crystals of Form I in contrast to the needle like habit of the crystals of Form II; as is illustrated by attached FIG. 3 and FIG. 4.

One of the main disadvantages of the needle-like crystals of Form II mentioned in WO 00/32189 is their low bulk density. It was found, that the crystals of the invention's Form I are distinctly denser in comparison to the crystals of Form II prepared according to the methods as given in International Applications WO 95/15316 and WO 96/37476. The following densities are typical and characteristic for the crystals of Form I and II, respectively:

|  | Form I | Form II |
|---|---|---|
| bulk density | ≧ about 0.270 g/ml | about 0.130 g/ml |
| tap density | ≧ about 0.360 g/ml | about 0.180 g/ml |

Consequently, the crystals of Form I are denser than the crystals of Form II, providing improved filtration and drying characteristics. Due to its increased density, better flow properties and lower electrostatic charge, Form I provides further advantages in formulation and capsule preparation.

The present invention further relates to a method for the production of the crystals of Form I of celecoxib by reacting 1-(4-methylphenyl)-4,4,4-trifluorobutane-1,3-dione of formula II (II)

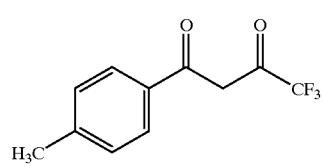

with 4-sulphonamidophenylhydrazine hydrochloride in a suitable solvent, crystallizing the resulting 4-[5-(4- methylphenyl)-3-(trifluoromethyl)-1H-pyrazol-1-yl]benzenesulfonamide from the reaction mixture and recrystallizing it from a suitable solvent. 1-(4-methylphenyl)-4,4,4-trifluorobutane-1,3-dione may be prepared according to Example 2 Step 1 in International Application WO 95/15316.

The preparation of celecoxib, according to the present invention, differs from the production described in WO 95/15316 mainly by the crystallization system used.

Thus, the dione is preferably reacted with 4-sulphonamidophenylhydrazine hydrochloride in isopropanol, instead of absolute ethanol, at reflux temperature. The reaction mixture is treated with activated carbon; after filtering, the product is preferably obtained by crystallizing it by the addition of a non-solvent, especially water (instead of by concentration of the reaction mixture). Finally, the substance is preferably recrystallized from isopropanol and water, instead of methylenechloride/hexane.

Accordingly, the present invention provides further advantages for the preparation of celecoxib by eliminating methylene chloride, a risk for the environment and human health. In addition, it also eliminates the use of n-hexane which causes an ignition and fire risk due to its electrostatic charge accumulation property. Further, according to the present invention, water replaces n-hexane. The use of isopropanol is a further advantage, since it is commercially available and widely used in chemical industry compared to absolute ethanol. Isopropanol should be anhydrous and may be combined with other hydroxylic solvents. Finally, by precipitating the product from the reaction mixture instead of concentrating the reaction mixture to dryness, a higher purity is achieved.

In order to obtain crystals of Form I, celecoxib is most preferably prepared by dissolving celecoxib in a suitable solvent system comprising at least one amide solvent, preferably selected from the group comprising N,N-dimethylformamide, NN-dimethylacetamide and/or mixtures thereof, N,N-dimethylfornamide being most preferred, from which solution the crystals of Form I are obtained by the addition of a non-solvent, especially water.

This recrystallization is generally carried out at temperatures of 0 to 80° C., particularly of 5 to 70° C., preferably of 10 to 60° C., more preferably of 15 to 50° C., preferably of 20 to 40° C., e.g., of 25 to 30° C. and/or ambient temperature.

The present invention further includes crystalline celecoxib of Form I crystallography, obtainable by the above described method of production. Further, the present invention includes pharmaceutical preparations, comprising crystalline celecoxib according to the present invention. Pharmaceutical preparations according to the present invention may be adapted for oral administration and are conveniently presented in the form of, e.g., tablets, capsules, dragees or the like. The formulations may contain ingredients like pharmaceutically acceptable carriers, excipients, adjuvants, etc. as they are known in the art.

EXAMPLE

Step a 1-(4-methylphenyl)-4,4,4-trifluorobutane-1,3-dione

4'-Methylacetophenone was dissolved in methanol (25 ml) under nitrogen atmosphere. To the stirred solution was added 25% sodium methoxide in methanol (12 ml). The reaction mixture was stirred for 5 minutes and ethyltrifluoroacetate (5.5 ml) was added. After refluxing under nitrogen atmosphere for 24 hours the mixture was cooled to room temperature and concentrated. 10% hydrochloric acid (100 ml) was added. The mixture was extracted with ethyl acetate (4×75 ml). The combined organic layer was dried over MgSO$_4$, filtered and concentrated. The product was obtained as an oily residue.

Step b

4-[5-(4-Methylphenyl)-3-(trifluoromethyl)-1H-pyrazol-1-yl]benzenesulfonamide 1-(4-Methylphenyl)-4,4,4-trifluorobutane-1,3-dione (4.14 g) from step a was stirred in isopropanol (75 ml). 4-sulphonamidophenylhydrazine hydrochloride (4.25 g) was added. The reaction mixture was refluxed under nitrogen atmosphere for 24 hours, cooled to room temperature and filtered, The filtrate was treated with activated carbon at 40–45° C. The product was crystallized by adding water (150 ml). The product was recrystallized from isopropanol and water.

Step c

Isolation of Form I

4-[5-(4-Methylphenyl)-3-(trifluoromethyl)-1H-pyrazol-1-yl]benzenesulfonamide (20 g) from step b was dissolved in N,N-dimethylformamide (80 ml) at room temperature. The product was crystallized by addition of water (200 ml). The reaction mixture was stirred for 30 minutes. The product was isolated by filtration, washed with water (3×40 ml) and dried. Yield: 18 g.

The product corresponds to FIG. 3 and showed the X-ray diffraction data presented in FIG. 1 and tables I and II.

It will thus be seen that the objects set forth above, among those made apparent from the preceding description, are efficiently attained and, since certain changes may be made in carrying out the above method (process) and in the composition set forth without departing from the spirit and scope of the invention, it is intended that all matter contained in the above description and shown in the accompanying drawing(s) shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

What is claimed is:

1. Crystalline 4-[5-(4-Methylphenyl)-3-(trifluoromethyl)-1H-pyrazol-1-yl]benzenesulfonamide, characterised by at least the following X-ray powder diffractogram reflexes:

| Angle [° 2θ] | Rel. int [%] |
| --- | --- |
| 14.800 | 69.0 |
| 16.050 | 78.9 |
| 17.875 | 63.7 |
| 19.615 | 100.0 |
| 21.455 | 96.6 |
| 22.080 | 68.1 |
| 22.385 | 65.4 |
| 23.425 | 62.5 |
| 25.330 | 64.5 |
| 29.355 | 60.8 |

2. The crystalline 4-[5-(4-Methylphenyl)-3-(trifluoromethyl)-1H-pyrazol-1-yl]benzenesulfonamide according to claim 1, characterised by at least the following further X-ray powder diffractogram reflexes:

| Angle [°2θ] | Rel. int [%] |
| --- | --- |
| 10.670 | 33.4 |
| 10.970 | 34.0 |
| 12.985 | 32.4 |
| 13.855 | 17.5 |
| 18.340 | 40.4 |
| 18.685 | 40.0 |
| 20.425 | 19.1 |
| 20.670 | 19.0 |
| 23.185 | 48.7 |
| 24.510 | 37.8 |
| 24.930 | 34.5 |
| 25.730 | 22.8 |
| 26.915 | 23.1 |
| 27.630 | 31.5 |
| 28.185 | 26.2 |
| 29.955 | 32.7 |
| 30.375 | 9.9 |
| 31.405 | 9.6 |
| 34.915 | 15.7 |
| 35.585 | 10.9 |
| 37.895 | 17.9 |
| 44.070 | 9.4 |
| 45.250 | 14.5. |

3. The crystalline 4-[5-(4-Methylphenyl)-3-(trifluoromethyl)-1H-pyrazol-1-yl]benzenesulfonamide according to claim 1, characterised in that it has a tap density of not less than 0.360 g/ml, and/or a bulk density of not less than 0.270 g/ml.

4. A method for the production of the crystalline substance of claim 1, comprising reacting 1-(4-methylphenyl)-4,4,4-trifluorobutane-1,3-dione with 4-sulphonamidophenylhydrazine hydrochloride in a suitable solvent, crystallizing the resulting 4-[5-(4-methylphenyl)-3-(trifluoromethyl)-1H-pyrazol-1-yl]benzenesulfonamide from the reaction mixture, and recrystallizing by solvent precipitation from a suitable solvent.

5. The method according to claim 4, comprising carrying out the reaction in isopropanol.

6. The method according to claim 4, comprising: crystallizing 4-[5-(4-methylphenyl)-3-(trifluoromethyl)-1H-pyrazol-1-yl]benzenesulfonamide from the reaction mixture by the addition of a non-solvent.

7. The method according to claim 6, wherein the non-solvent, is water.

8. The method according to claim 4, comprising:
    crystallizing 4-[5-(4-methylphenyl)-3-(trifluoromethyl)-1H-pyrazol-1-yl]benzenesulfonamide from a solvent system including at least one amide solvent.

9. The method according to claim 4, comprising, recrystallizing 4-[5-(4-methylphenyl)-3-(trifluoromethyl)-1H-pyrazol-1-yl]benzenesulfonamide from a solvent system including at least one amide solvent by adding a non-solvent, at a temperature between about 0° C. and 80° C.

10. The method according to claim 9, wherein the non-solvent is water.

11. The method according to claim 8, the amide solvent is selected from the group wherein consisting of N,N-dimethylformamide, N,N-dimethylacetamide and mixtures thereof.

12. Crystalline 4-[5-(4-methylphenyl)-3-(trifluoromethyl)-1H-pyrazol-1-yl]benzenesulfonamide prepared by the method of any one of claims 4 to 11.

13. A pharmaceutical prepartion, comprising crystalline 4-[5-(4-methylphenyl)-3-(trifluoromethyl)-1H-pyrazol-1-yl]benzenesulfonamide in accordance with any one of claims 1, 2 or 3.

14. A pharmaceutical preparation, comprising crystalline 4-[5-(4-methylphenyl)-3-(trifluoromethyl)-1H-pyrazol-1-yl]benzenesulfonamide prepared by the method of any of claims 4 to 11.

\* \* \* \* \*